(12) United States Patent
Shibata et al.

(10) Patent No.: US 11,955,211 B2
(45) Date of Patent: Apr. 9, 2024

(54) FIRST-AID INFORMATION PROVISION SYSTEM, INFORMATION DISPLAY DEVICE, INFORMATION OUTPUT DEVICE, FIRST-AID INFORMATION PROVISION METHOD, AND RECORDING MEDIUM

(71) Applicant: NEC Corporation, Tokyo (JP)

(72) Inventors: Takashi Shibata, Tokyo (JP); Shoji Yachida, Tokyo (JP); Chisato Funayama, Tokyo (JP); Masato Tsukada, Tokyo (JP); Yuka Ogino, Tokyo (JP); Keiichi Chono, Tokyo (JP); Emi Kitagawa, Tokyo (JP); Yasuhiko Yoshida, Tokyo (JP); Yusuke Mori, Tokyo (JP); Toru Takahashi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 392 days.

(21) Appl. No.: 17/282,520

(22) PCT Filed: Oct. 15, 2018

(86) PCT No.: PCT/JP2018/038242
§ 371 (c)(1),
(2) Date: Apr. 2, 2021

(87) PCT Pub. No.: WO2020/079719
PCT Pub. Date: Apr. 23, 2020

(65) Prior Publication Data
US 2021/0358580 A1    Nov. 18, 2021

(51) Int. Cl.
*G16H 10/60*    (2018.01)
*G06F 16/532*    (2019.01)
(Continued)

(52) U.S. Cl.
CPC ........... *G16H 10/60* (2018.01); *G06F 16/532* (2019.01); *G06K 7/1413* (2013.01); *G06V 40/19* (2022.01); *G06F 21/32* (2013.01); *G06K 7/1417* (2013.01)

(58) Field of Classification Search
CPC ....... G16H 10/60; G06F 16/532; G06F 21/32; G06F 21/6245; G06K 7/1413;
(Continued)

(56) References Cited

U.S. PATENT DOCUMENTS 5,071,168 A * 12/1991 Shamos .................. G07C 9/27
283/117
2002/0128864 A1* 9/2002 Maus ...................... G16H 40/63
705/2
(Continued)

FOREIGN PATENT DOCUMENTS

JP    2003-085148 A    3/2003
JP    2004152046 A *  5/2004
(Continued)

OTHER PUBLICATIONS

JP2004152046A, Nakamura et al. Machine translation (Year: 2004).*
(Continued)

*Primary Examiner* — Fernando Alcon
(74) *Attorney, Agent, or Firm* — Sughrue Mion, PLLC

(57) ABSTRACT

A first-aid information provision system of the example embodiments includes: an information display device that includes first capture means for capturing an iris image, code acquisition means for acquiring a code associated with the captured iris image, and code display means for displaying the acquired code; and an information output device that includes second capture means for imaging the code displayed by the information display device, first-aid information acquisition means for acquiring first-aid information
(Continued)

about an individual associated with the iris image by using the imaged code, and first-aid information output means for outputting the first-aid information.

12 Claims, 8 Drawing Sheets

(51) Int. Cl.
*G06F 21/32* (2013.01)
*G06K 7/14* (2006.01)
*G06V 40/19* (2022.01)

(58) Field of Classification Search
CPC .. G06K 7/1417; G06V 40/19; H04L 63/0861; H04W 12/06; H04W 12/77
See application file for complete search history.

(56) References Cited

U.S. PATENT DOCUMENTS

| | | | |
|---|---|---|---|
| 2008/0025575 A1* | 1/2008 | Schonberg | G06V 40/193 |
| | | | 382/117 |
| 2009/0006439 A1 | 1/2009 | Joseph et al. | |
| 2010/0183199 A1* | 7/2010 | Smith | H04L 9/3231 |
| | | | 707/769 |
| 2011/0015945 A1* | 1/2011 | Addy | G16H 20/10 |
| | | | 235/487 |
| 2012/0148115 A1* | 6/2012 | Birdwell | G06F 18/00 |
| | | | 382/116 |
| 2013/0197941 A1 | 8/2013 | Cochran | |
| 2014/0063055 A1* | 3/2014 | Osterhout | G02B 27/017 |
| | | | 345/633 |
| 2014/0122053 A1* | 5/2014 | Lotan | G16H 10/60 |
| | | | 704/270.1 |
| 2015/0205919 A1 | 7/2015 | Robertson | |
| 2015/0213208 A1* | 7/2015 | Zhang | A61B 5/0205 |
| | | | 600/490 |
| 2015/0223057 A1* | 8/2015 | Dellarciprete | G06F 21/6245 |
| | | | 455/410 |
| 2016/0260002 A1* | 9/2016 | Hill | H04L 9/14 |
| 2017/0264608 A1 | 9/2017 | Moore et al. | |
| 2019/0268158 A1* | 8/2019 | Lentini | H04L 9/30 |
| 2020/0294634 A1* | 9/2020 | Katz | G16H 50/30 |

FOREIGN PATENT DOCUMENTS

| | | | |
|---|---|---|---|
| JP | 2007-034798 A | 2/2007 | |
| JP | 2007-241914 A | 9/2007 | |
| JP | 2017-208135 A | 11/2017 | |
| WO | WO-0031677 A1 * | 6/2000 | ......... G07C 9/00158 |

OTHER PUBLICATIONS

Extended European Search Report for EP Application No. EP18936884.8 dated Sep. 23, 2021.
International Search Report for PCT Application No. PCT/JP2018/038242, dated Jan. 8, 2019.
English translation of Written opinion for PCT Application No. PCT/JP2018/038242, dated Jan. 8, 2019.
U.S. Office Action for U.S. Appl. No. 17/680,546, dated Aug. 9, 2023.

* cited by examiner

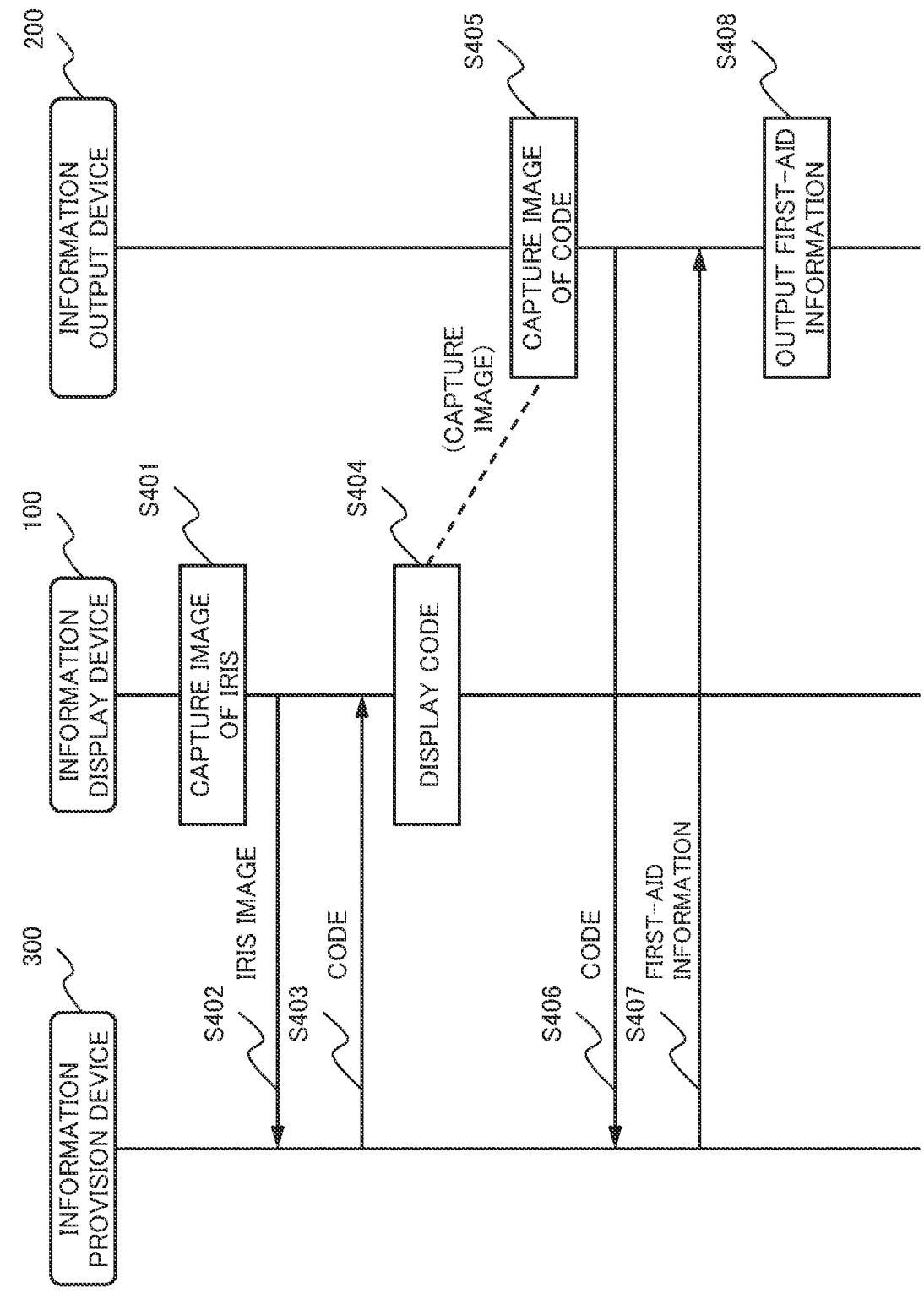

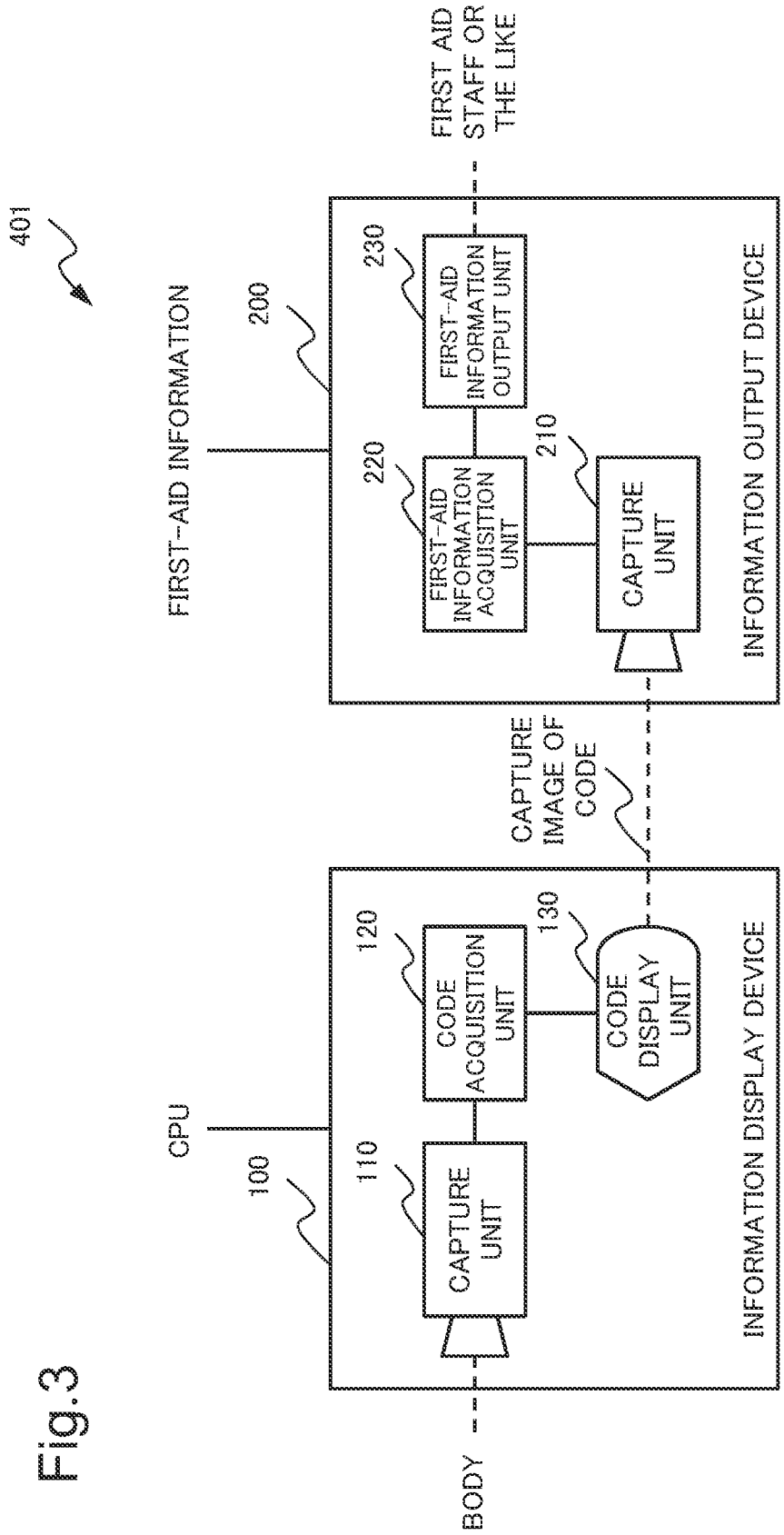

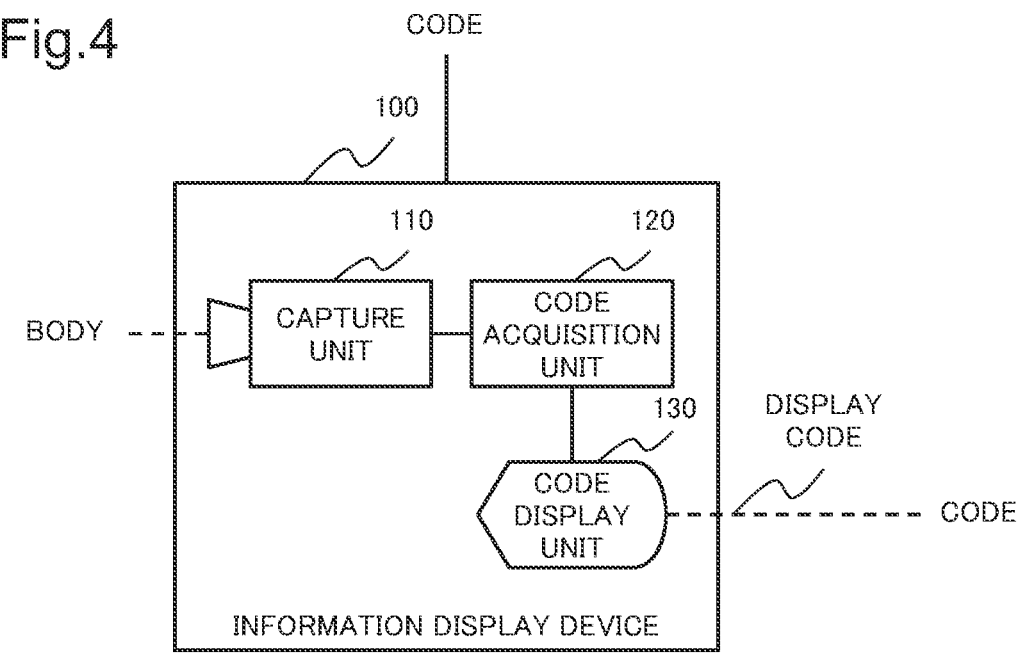
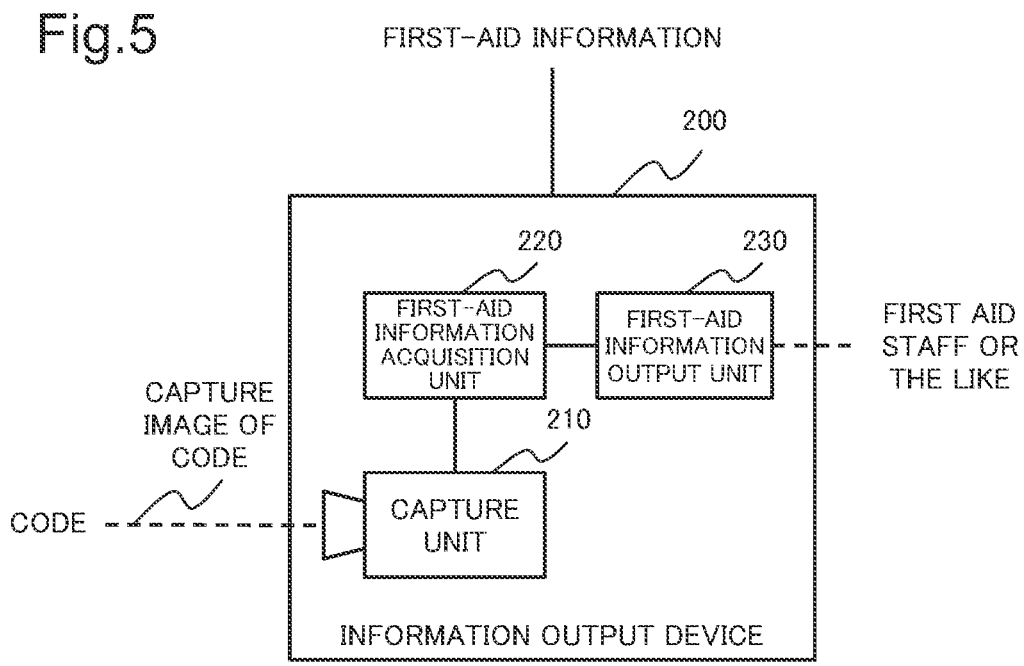

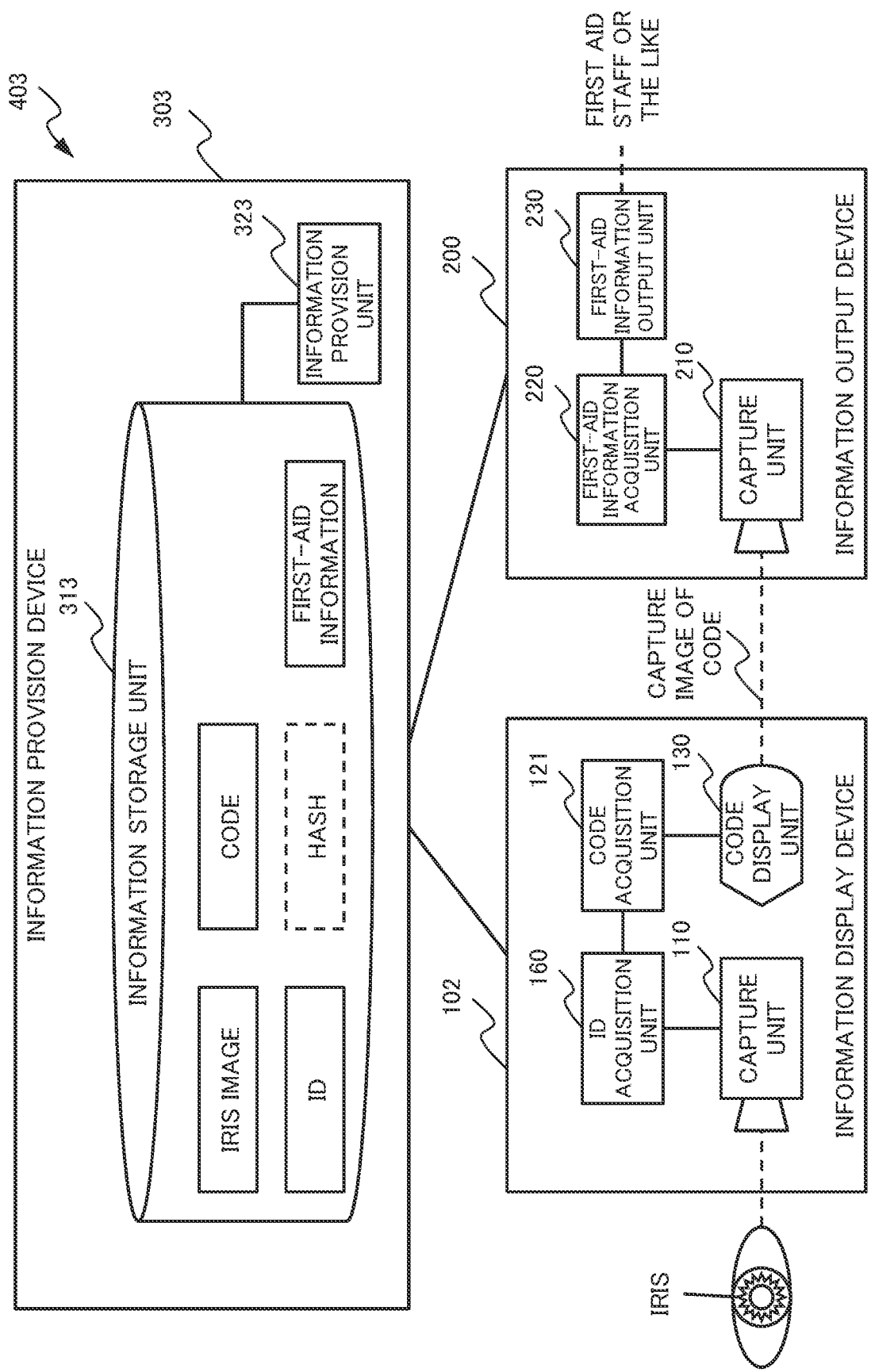

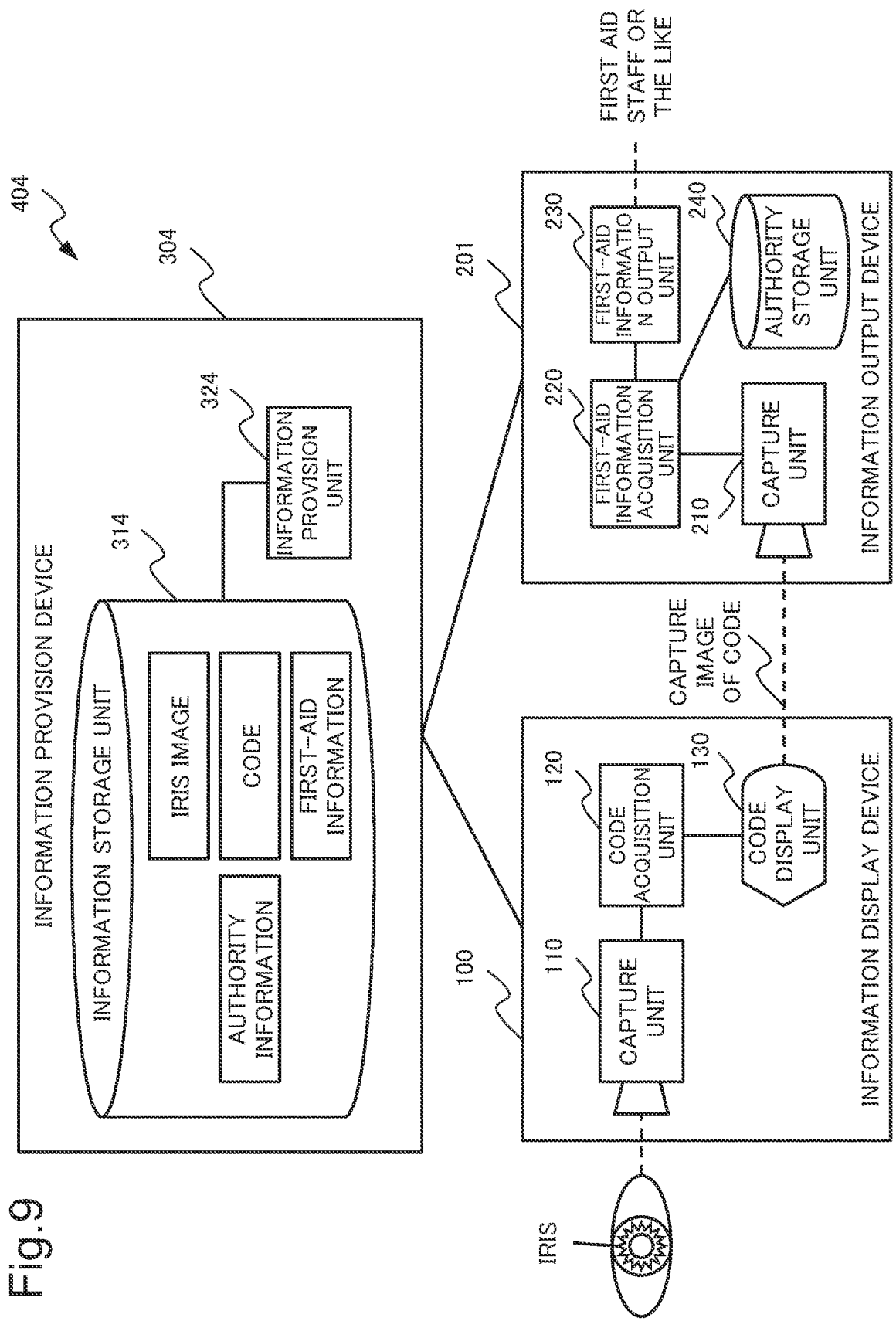

FIRST-AID INFORMATION PROVISION SYSTEM, INFORMATION DISPLAY DEVICE, INFORMATION OUTPUT DEVICE, FIRST-AID INFORMATION PROVISION METHOD, AND RECORDING MEDIUM

This application is a National Stage Entry of PCT/JP2018/038242 filed on Oct. 15, 2018, the contents of all of which are incorporated herein by reference, in their entirety.

TECHNICAL FIELD

The example embodiments relates to an information processing system related to first aid and the like, and more particularly to a first-aid information provision system for providing information used for first aid.

BACKGROUND ART

With the spread of smartphones and the like, it has become easier to obtain necessary information via networks.

For example, technologies using a mobile terminal carried by an individual for providing information have been proposed (see, for example, PTLs 1 and 2).

An information acquisition mobile terminal device described in PTL 1 outputs, on the basis of individual identification information and system identification information of a medical institution or the like, in-system user identification information associated with the individual identification information and the system identification information. The in-system user identification information is, for example, medication history information. For example, a patient uses a device that the patient carries to acquire a medicine at a pharmacy or the like.

A rescue information system described in PTL 2 has a communication terminal and a server. The communication terminal transmits, to the server, authentication information input by a user. The server transmits, to the communication terminal, a result of determination as to whether the authentication information is appropriate. When a determination that the authentication information is appropriate is received from the server, the communication terminal transmits, to the server, a request to transmit personal information. The server transmits, to the communication terminal, the personal information in response to the transmission request. When the personal information is received from the server, a terminal device outputs the personal information.

CITATION LIST

Patent Literature

[PTL 1] JP 2017-208135 A
[PTL 2] JP 2007-034798 A

SUMMARY

Technical Problem

The inventions described in PTLs 1 and 2 described above assume that an owner of a mobile terminal operates the mobile terminal or the like.

However, victims of accidents and the like are not always able to operate their mobile terminals. For example, an unconscious person cannot operate the mobile terminal.

That is, in the inventions described in PTLs 1 and 2, information cannot be acquired in a case where the owner cannot operate the mobile terminal.

In PTLs 1 and 2, in a case where mobile terminals can be operated by a third party, a mobile terminal of an unconscious person or the like can be used for provision of information. However, in the case where mobile terminals can be operated by a third party, information leakage occurs in the absence of the owner of the mobile terminal due to, for example, theft of the mobile terminal.

In particular, medical information is sensitive information, and it is highly necessary to avoid output of the information to unspecified majority.

In this way, the inventions described in PTLs 1 and 2 have a problem in that, for provision of information when the owner cannot operate the device, information cannot be protected when the owner is not present. Alternatively, the inventions described in PTLs 1 and 2 have a problem in that, for protection of information when the owner is not present, information cannot be provided when the owner cannot operate the device.

It is an object of the example embodiments to solve the problems described above and provide a first-aid information provision system or the like that provides information even in a case where an owner cannot operate a device and refrains from providing information when the owner is not present.

Solution to Problem

According to a first mode of the example embodiments, there is provided a first-aid information provision system including:

an information display device that includes first capture means for capturing an iris image, code acquisition means for acquiring a code associated with the captured iris image, and code display means for displaying the acquired code; and an information output device that includes second capture means for imaging the code displayed by the information display device, first-aid information acquisition means for acquiring first-aid information about an individual associated with the iris image by using the imaged code, and first-aid information output means for outputting the first-aid information.

According to the first mode of the example embodiments, there is provided an information display device including:

first capture means for capturing an iris image;

code acquisition means for acquiring a code associated with the captured iris image; and code display means for displaying the acquired code as the code imaged by an information output device that captures the code, acquires first-aid information about an individual associated with the iris image by using the imaged code, and outputs the first-aid information.

According to the first mode of the example embodiments, there is provided an information output device including:

second capture means for imaging a code displayed by an information display device that captures an iris image, acquires the code associated with the captured iris image, and displays the acquired code;

first-aid information acquisition means for acquiring first-aid information about an individual associated with the iris image by using the imaged code; and first-aid information output means for outputting the first-aid information.

According to the first mode of the example embodiments, there is provided a first-aid information provision method in a first-aid information provision system that includes an information display device and an information output device, the method including:

by the information display device, capturing an iris image;

acquiring a code associated with the captured iris image; and displaying the acquired code, and by the information output device, imaging the code displayed by the information display device;

acquiring first-aid information about an individual associated with the iris image by using the imaged code; and outputting the first-aid information.

According to a second mode of the example embodiments, there is provided a first-aid information provision method including:

by an information display device, capturing an iris image;

acquiring a code associated with the captured iris image; and displaying the acquired code as the code to be imaged by an information output device that captures the code, acquires first-aid information about an individual associated with the iris image by using the imaged code, and outputs the first-aid information.

According to a third mode of the example embodiments, there is provided a first-aid information provision method including:

imaging a code displayed by an information display device that captures an iris image, acquires the code associated with the captured iris image, and displays the acquired code;

acquiring first-aid information about an individual associated with the iris image by using the imaged code; and outputting the first-aid information.

According to the first mode of the example embodiments, there is provided a recording medium that records a program that causes an information display device to execute:

processing of capturing an iris image;

processing of acquiring a code associated with the captured iris image; and processing of displaying the acquired code as the code imaged by an information output device that captures the code, acquires first-aid information about an individual associated with the iris image by using the imaged code, and outputs the first-aid information.

According to the second mode of the example embodiments, there is provided a recording medium that records a program that causes an information processing device to execute:

processing of imaging a code displayed by an information display device that captures an iris image, acquires the code associated with the captured iris image, and displays the acquired code;

processing of acquiring first-aid information about an individual associated with the iris image by using the imaged code; and processing of outputting the first-aid information.

Advantageous Effects

The example embodiments has an effect of providing information even in a case where the owner cannot operate the device, and refraining from providing information when the owner is not present.

BRIEF DESCRIPTION OF DRAWINGS

FIG. 2 is a sequence diagram illustrating an example of an operation of the first-aid information provision system according to the first example embodiment.

FIG. 3 is a block diagram illustrating an example of the configuration of the first-aid information provision system as an outline of the first example embodiment.

FIG. 4 is a block diagram illustrating an example of an outline of an information display device according to the first example embodiment.

FIG. 5 is a block diagram illustrating an example of an outline of an information output device according to the first example embodiment.

FIG. 8 is a block diagram illustrating an example of a configuration of a first-aid information provision system according to a third example embodiment.

FIG. 9 is a block diagram illustrating an example of a configuration of a first-aid information provision system according to a fourth example embodiment.

EXAMPLE EMBODIMENT

Figure 1:
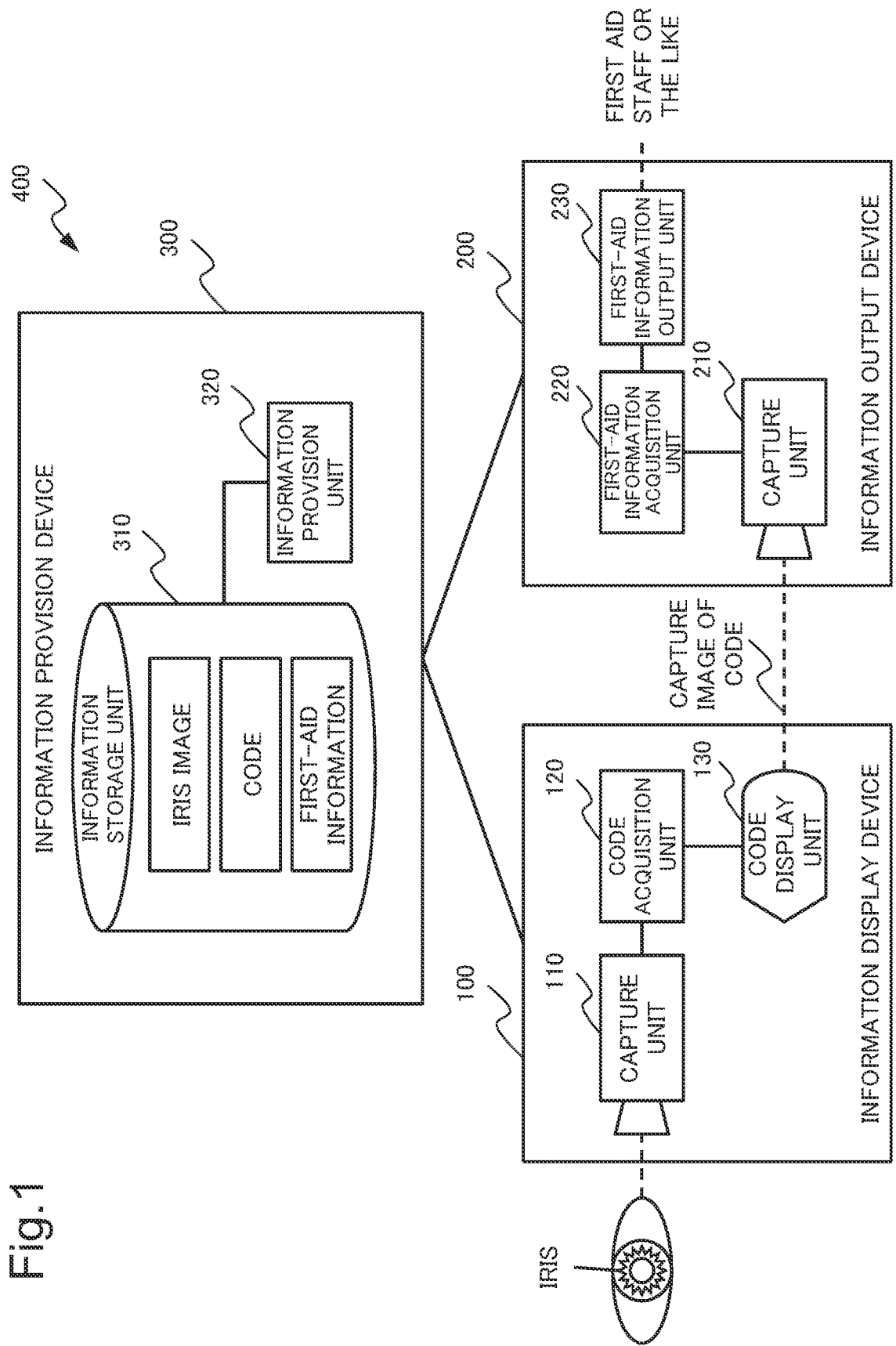
FIG. 1 is a block diagram illustrating an example of a configuration of a first-aid information provision system according to a first example embodiment.

Next, example embodiments will be described with reference to the drawings.

The drawings are for describing the example embodiments. However, the example embodiments is not limited to the descriptions in the drawings. Similar configurations in the drawings may be denoted by the same reference numerals, and the repeated description thereof may be omitted. In the drawings used in the following description, configurations not related to the description of the example embodiments may be omitted from the description, and may not be illustrated.

Physical characteristics specific to an individual (hereinafter referred to as "biometrics") used in each example embodiment are not restrictive. For example, biometrics includes fingerprints, blood vessels, irises, or a combination thereof. In the following description, "irises" are used by way of example. However, this is not intended to limit the target of each example embodiment to irises. In each example embodiment, the biometrics to be used is not restrictive.

Information regarding biometrics (biometric information) may be in a plurality of forms of information such as images or voices. In the following description, an image (specifically, an iris image) is used by way of example of the biometric information, but this is not intended to limit each example embodiment.

Each example embodiment uses a code generated in accordance with the biometric information (iris image). The code may be a one-dimensional code (e.g., a bar code) or a two-dimensional code (e.g., a QR code (registered trademark)). Alternatively, the code may use information associated to three dimensions such as a hologram. In this way, the code is a numerical value converted into a predetermined shape.

In each example embodiment, codes may be generated by a generation method that conforms to specifications of each code.

By way of example, in a case of a bar code, the code is generated by an operation as described below. An image to be converted into a code is converted into binary (0 and 1) continuous data (serial data). In order from either side (the highest or lowest order) of the data, each of "0" and "1" is converted into codes as follows. As for "0", the number of consecutive "0"s (in the range from one to four) is converted into an associated one of four predetermined kinds of spaces (white rectangle). As for "1", the number of consecutive "1"s (in the range from one to four) is converted into an associated one of four predetermined kinds of bars (black rectangle). To a code that is a combination of rectangles created in this way, a predetermined code (left and right guard bars, a center bar, and left and right margins) is added, and thus a bar code is obtained.

Applications for generating bar codes and the like are widely provided. Thus, such applications can be used in the example embodiments.

Note that, in the example embodiments, the format of the code used is not limited to that described above.

It is preferable that the code be information in which the amount of information has been reduced enough to prevent inference of biometric information from the code.

This is for the following reasons.

The code is information that is imaged and communicated for the purpose of providing information. First-aid information is acquired multiple times in some cases. Thus, the code is information that may be imaged and communicated multiple times. As the number of times of imaging and communication increases, the information is more likely to be leaked to a third party. For this reason, in order to prevent leakage of biometric information, it is preferable that the code be information from which biometric information cannot be inferred.

Reducing the amount of information generally results in reducing the amount of data. Thus, as compared to communication of biometric information, communication of codes reduces a load of communication between devices. Moreover, processing of codes requires less processing load than processing of biometric information.

Furthermore, the code may include another piece of information in addition to biometric information.

The example embodiments provide information related to first aid (first-aid information). Note that individuals targeted for first aid, the contents of first aid, and the first-aid information in the example embodiments are not restrictive.

The targeted individuals are people in need of help. For example, the individuals include injured persons, unconscious persons, infants, elderly persons, and/or persons with disabilities.

The first aid is an operation for helping the persons described above. For example, the first aid includes assistance to help with daily life, guiding a lost child, medical treatment for an injured person, first-aid activities in a disaster, or identity confirmation and transfer of an unconscious person. The above is examples, and there is no limitation on the contents of first aid in the example embodiments.

The first-aid information is information used to provide first aid to the targeted individuals. The first-aid information is, for example, contact information such as an address, a telephone number, or an email address, or medical information such as allergies and/or medication history.

First Example Embodiment

A first example embodiment will be described below with reference to the drawings.
[Description of Configuration]
First, a configuration of a first-aid information provision system 400 according to the first example embodiment will be described with reference to the drawings.

FIG. 1 is a block diagram illustrating an example of the configuration of the first-aid information provision system 400 according to the first example embodiment.

The first-aid information provision system 400 includes an information display device 100, an information output device 200, and an information provision device 300.

FIG. 1 illustrates one each of the devices included in the first-aid information provision system 400. However, this is for clarity of the drawing, and is not intended to limit the number of pieces of each device included in the first-aid information provision system 400. The number of pieces of each device included in the first-aid information provision system 400 is not limited to one. For example, the first-aid information provision system 400 may include a plurality of the information output devices 200.

The information display device 100 is connected to the information provision device 300 via a communication path. The information output device 200 is connected to the information provision device 300 via a communication path. The communication paths described above may be or may not be in the same network.

The information provision device 300 provides information to the information display device 100 and the information output device 200 via the communication paths.

There is no limitation on the source of the information provided by the information provision device 300. For example, the information provision device 300 may provide information by acquiring information from a device (not illustrated) and providing the acquired information.

However, for convenience of description, the following description assumes that the information provision device 300 stores information in advance.

The information provision device 300 may authenticate the information display device 100 and/or the information output device 200.

For example, as will be described later, the information provision device 300 receives an iris image from the information display device 100. For this reason, the information provision device 300 may use the received iris image to determine whether a request has been made by a legitimate person (e.g., an owner of the information display device 100).

The information display device 100 captures an iris, acquires a code associated with the imaged iris from the information provision device 300, and displays the acquired code.

The information output device 200 captures the code displayed by the information display device 100, acquires first-aid information associated with the imaged code from the information provision device 300, and outputs (e.g., transmits, to an external display device) the acquired first-aid information.

In a case where the first-aid information provision system 400 is applied to an emergency hospital, for example, each device operates as follows.

The information provision device 300 is a device for managing regional medical information. The information provision device 300 stores necessary information (e.g., first-aid information) in advance.

The information display device 100 is a device carried by a victim of an accident.

An emergency hospital doctor or nurse (hereinafter referred to as the doctor or the like) captures an image of the victim's iris by using the information display device 100 (e.g., a mobile phone) carried by the victim. Furthermore, the doctor or the like operates the information display device 100 to acquire a code associated with the captured iris image from the information provision device 300, and the code is displayed on the information display device 100. For example, the doctor or the like holds down a button or the like to image the iris of the victim, and the code associated with the imaged iris is displayed on the information display device 100.

Then, the doctor or the like captures the displayed code by the information output device 200. The information output device 200 acquires first-aid information (e.g., medication history) associated with the imaged code from the information provision device 300, and causes a display device to display the first-aid information.

The doctor or the like refers to the displayed first-aid information, and treats the victim.

An emergency hospital is an example of a facility in which the information output device 200 is installed. The facility where the information output device 200 is installed is not limited to an emergency hospital. For example, the facility in which the information output device 200 is installed is a health center, a government office, an airport, a police station, or an amusement park.

The information provision device 300 may be an external device of the first-aid information provision system 400. In this case, the first-aid information provision system 400 may acquire information from the external device corresponding to the information provision device 300 as necessary.

Next, a detailed configuration of each device will be described.

The information provision device 300 includes an information storage unit 310 and an information provision unit 320.

The information storage unit 310 stores information used by the information display device 100 and the information output device 200. For pieces of information that need to be associated with each other, the information storage unit 310 stores them in association with each other.

For example, in the description of the present example embodiment, the information storage unit 310 stores the following information.

The information storage unit 310 stores an iris image and a code in association with each other. Furthermore, the information storage unit 310 stores a code and a piece of first-aid information in association with each other.

As long as the information storage unit 310 stores necessary information before a request from the information display device 100 or the like, there is no limitation on the timing for storing the information and the like. The information storage unit 310 does not limit a transmission source that transmits information. The information provision device 300 may receive information from a related device (e.g., a medical institution or a public institution (government agency or government office)) and store the information in advance.

The information storage unit 310 may store the pieces of information described above as a lump of information. Alternatively, the information storage unit 310 may store the pieces of information described above as a set of two or more pieces of information. In this case, the information storage unit 310 may be constituted by a plurality of configurations or devices. For example, the information storage unit 310 may be constituted by a configuration for storing an iris image and a code in association with each other (first storage unit) and a configuration for storing a code and a piece of first-aid information in association with each other (second storage unit). Alternatively, the information provision device 300 may be configured as a combination of a device that includes the first storage unit described above and a device that includes the second storage unit described above.

In accordance with an instruction from the information display device 100 and the information output device 200, the information provision unit 320 uses associations between pieces of information to provide information related to the instruction from information stored in the information storage unit 310.

In a case where an instruction to provide a code associated with an iris image has been received from the information display device 100, the information provision unit 320 provides the information display device 100 with the code associated with the iris image included in the instruction from codes stored in the information storage unit 310. For the purpose of improving security in distribution of codes, the information provision device 300 may authenticate the information display device 100 that transmits codes.

However, iris images generated by the information display device 100 by using an iris of the same individual are not always the same.

For example, an iris image changes depending on the position of the iris with respect to the information display device 100. As a result, iris images of the same individual received by the information provision device 300 do not always match each other.

For this reason, in a determination as to whether an iris image received from the information display device 100 matches a stored iris image, the information provision unit 320 may accept an error within a predetermined range in addition to an identical match. For example, the information provision unit 320 may use matching of equal to or more than 95% for the iris image match determination. Alternatively, in a case where the information storage unit 310 stores a plurality of iris images, the information provision unit 320 may determine an iris image with the highest degree of matching as a matched iris image.

Furthermore, for the iris image match determination, the information provision unit 320 may use image processing such as image movement, rotation, enlargement, reduction, deformation, and combinations thereof.

The information provision device 300 may create a code on the basis of an iris image received from the information display device 100. In this case, the information provision device 300 may not include the information storage unit 310.

Alternatively, in a case where the information output device 200 has instructed the information provision unit 320 to provide first-aid information associated with a code, the information provision unit 320 provides the information output device 200 with the first-aid information associated with the code included in the instruction from first-aid information stored in the information storage unit 310. For the purpose of improving security in distribution of first-aid information, the information provision device 300 may authenticate the information output device 200 that transmits first-aid information.

As a method for generating a code from an iris image, a plurality of methods may be used. In this case, different codes may be generated depending on the method. For this reason, the information provision device 300 may store, as a code to be associated with a piece of first-aid information, a code for each method used by the first-aid information provision system 400.

Furthermore, for example, a code may include information that indicates a code generation method. In this case, the information provision unit 320 may select a code to be compared in consideration of the generation method included in the code.

The information provision unit 320 may use a predetermined acceptable range for code matching as in the iris image match determination.

The information display device 100 includes an capture unit 110 (hereinafter also referred to as the "first capture unit" as necessary), a code acquisition unit 120, and a code display unit 130.

The capture unit 110 captures an image of an iris to generate an iris image.

The code acquisition unit 120 uses the iris image captured by the capture unit 110 (first capture unit) to acquire a code associated with the iris from the information provision device 300.

The code display unit 130 displays the acquired code. For example, the code display unit 130 includes a liquid crystal display (not illustrated), and displays the code on the liquid crystal display. Alternatively, the code display unit 130 may display the code on an external device (not illustrated).

The information output device 200 includes an capture unit 210 (hereinafter also referred to as the "second capture unit" as necessary), a first-aid information acquisition unit 220, and a first-aid information output unit 230.

The capture unit 210 captures an image of a code displayed by the information display device 100, and outputs data of the captured image.

The first-aid information acquisition unit 220 uses the code from the image data to acquire first-aid information from the information provision device 300.

The first-aid information output unit 230 outputs the acquired first-aid information to a predetermined device for reference by first aid staff or the like. For example, the first-aid information output unit 230 may transmit first-aid information to a display device carried by first aid staff (not illustrated), and cause the display device to display the first-aid information. Alternatively, in a case where the information output device 200 includes a liquid crystal display (not illustrated), the first-aid information output unit 230 may display first-aid information on the liquid crystal display. First aid staff or the like uses the first-aid information displayed on the liquid crystal display to provide first aid.

Alternatively, the first-aid information output unit 230 may transmit information to a predetermined contact person in accordance with the received first-aid information. For example, in a case where the first-aid information includes a contact email address, the first-aid information output unit 230 may transmit a text related to first aid to the contact email address.

For example, in a case where a victim of an accident carries the information display device 100, the information output device 200 may acquire contact information of a family member or the like of the victim as first-aid information, and inform the family member or the like of the victim that the victim has been involved in the accident.

Alternatively, in a case where a lost child carries the information display device 100, the information output device 200 may send a message to a mobile device of the child's guardian.

The information output device 200 may store a fixed phrase in advance. In this case, the information output device 200 transmits the stored fixed phrase to the contact email address included in the first-aid information.

Capturing of an image of an iris described above may be performed by a person other than the owner of the information display device 100. For example, in a case where the owner of the information display device 100 has an injured arm or the like or is unconscious, the owner cannot operate the information display device 100. Thus, a hospital doctor or the like uses the information display device 100 to capture an image of an iris of the owner and displays a code. Then, the information output device 200 captures an image of the displayed code, and outputs first-aid information.

In this way, the first-aid information provision system 400 cannot acquire first-aid information in a case where the owner is not present because the information display device 100 uses an iris image of the owner or the like. On the other hand, in a case where the owner is present, another person can capture an image of the iris and acquire first-aid information.

[Description of operation]

Next, an operation of the first-aid information provision system 400 according to the first example embodiment will be described with reference to the drawings.

FIG. 2 is a sequence diagram illustrating an example of the operation of the first-aid information provision system 400 according to the first example embodiment.

The information provision device 300 stores necessary information in advance.

First, the information display device 100 captures an image of an iris (S401).

The information display device 100 transmits the iris image to the information provision device 300 (S402).

The information provision device 300 sends back a code associated with the iris image (S403).

The information display device 100 displays the received code (S404).

The information output device 200 captures the code (S405).

The information output device 200 transmits data of the imaged code to the information provision device 300 (S406).

The information provision device 300 sends back first-aid information associated with the code (S407).

The information output device 200 outputs (e.g., displays) the received first-aid information (S408).

The first-aid information provision system 400 may repeat the operations in S404 to S408 described above. A plurality of the information output devices 200 may execute the operations in S405 to S408.

[Description of Effects]

Next, effects of the first-aid information provision system 400 according to the first example embodiment will be described.

The first-aid information provision system 400 according to the first example embodiment can obtain an effect of providing information even in a case where the owner of the information display device 100 cannot operate the device, and refraining from providing information when the owner is not present.

This is because of the following reasons.

The first-aid information provision system 400 includes the information display device 100 and the information output device 200. The information display device 100 includes the capture unit 110 (first capture unit), the code acquisition unit 120, and the code display unit 130. The capture unit 110 captures an iris image. The code acquisition unit 120 acquires a code associated with the captured iris image. The code display unit 130 displays the acquired code. The information output device 200 includes the capture unit 210 (second capture unit), the first-aid information acquisition unit 220, and the first-aid information output unit 230. The capture unit 210 captures the code displayed by the information display device 100. The first-aid information acquisition unit 220 uses the imaged code to acquire first-aid information about an individual associated with the iris image. The first-aid information output unit 230 outputs the first-aid information.

The information provision device 300 provides information necessary in the above.

In the first-aid information provision system 400 described above, the information display device 100 displays a code by using an iris image of the owner of the information display device 100 or the like. Thus, the first-aid information provision system 400 cannot display the code in a case where the owner or the like is not present.

However, the information display device 100 does not necessarily need to be operated by the owner to display the code. That is, the first-aid information provision system 400 can display the code even in a case where the owner cannot operate the information display device 100.

The information output device 200 can output the first-aid information as many times as necessary by using the code displayed on the information display device 100. Furthermore, a plurality of the information output devices 200 can output the first-aid information as many times as necessary by using the code displayed on the information display device 100.

In this way, in the first-aid information provision system 400, when the information display device 100 has succeeded in acquiring an iris image, the information output device 200 outputs first-aid information. Thus, the first-aid information provision system 400 can protect the first-aid information in a case where the owner is not present, for example, in the event of theft.

Furthermore, the first-aid information provision system 400 uses the code displayed on the information display device 100, and this makes it possible to prevent leakage of the owner's iris image.

The first-aid information provision system 400 has no restrictions on display of a code displayed on the information display device 100. Thus, the first-aid information provision system 400 can provide first-aid information even in a case where the owner cannot operate the information display device 100.

[Outline of Example Embodiments]

Next, an outline of the first example embodiment will be described with reference to the drawings.

FIG. 3 is a block diagram illustrating an example of a configuration of a first-aid information provision system 401, which is the outline of the first example embodiment.

The first-aid information provision system 401 includes the information display device 100 and the information output device 200. The information display device 100 includes the capture unit 110 (first capture unit), the code acquisition unit 120, and the code display unit 130. The capture unit 110 captures an iris image. The code acquisition unit 120 acquires a code associated with the captured iris image. The code display unit 130 displays the acquired code. The information output device 200 includes the capture unit 210 (second capture unit), the first-aid information acquisition unit 220, and the first-aid information output unit 230. The capture unit 210 captures the code displayed by the information display device 100. The first-aid information acquisition unit 220 uses the imaged code to acquire first-aid information about an individual associated with the iris image. The first-aid information output unit 230 outputs the first-aid information.

The information display device 100 and the information output device 200 are connected to a device corresponding to the information provision device 300 (not illustrated) to acquire information. As described above, each configuration included in the first-aid information provision system 401 operates in a similar manner to the relative configuration in the first-aid information provision system 400.

The first-aid information provision system 401 configured in this way can obtain effects similar to those of the first-aid information provision system 400.

This is because each configuration in the first-aid information provision system 401 operates in a similar manner to the similar configuration in the first-aid information provision system 400. That is, the first-aid information provision system 401 can provide first-aid information in accordance with a code displayed by using an iris image.

The first-aid information provision system 401 is an example of a minimum configuration of the first-aid information provision system 400 in the first example embodiment.

FIG. 4 is a block diagram illustrating an example of an outline of the information display device 100 according to the first example embodiment.

The information display device 100 includes the capture unit 110 (first capture unit), the code acquisition unit 120, and the code display unit 130. The capture unit 110 captures an iris image. The code acquisition unit 120 acquires a code associated with the captured iris image. The code display unit 130 displays an acquired code as a code to be imaged by a device corresponding to the information output device 200. The device corresponding to the information output device 200 captures the code, uses the imaged code to acquire first-aid information about an individual associated with the iris image, and outputs the first-aid information.

The information display device 100 illustrated in FIG. 4 includes similar configurations to the information display device 100 illustrated in FIG. 1. The information display device 100 is connected to a device having similar functions to the information provision device 300.

The information display device 100 configured in this way uses each configuration to display a code by using an iris image of the owner of the information display device 100 or the like.

This is because each configuration in the information display device 100 illustrated in FIG. 4 operates in a similar manner to the configuration in the information display device 100 described with reference to FIG. 1.

The information display device 100 illustrated in FIG. 4 is an example of a minimum configuration of the information display device 100 in the first example embodiment.

FIG. 5 is a block diagram illustrating an example of an outline of the information output device 200 according to the first example embodiment.

The information output device 200 includes the capture unit 210 (second capture unit), the first-aid information acquisition unit 220, and the first-aid information output unit 230. The capture unit 210 captures a code displayed by a device corresponding to the information display device 100. The device corresponding to the information display device 100 captures an iris image, acquires a code associated with the captured iris image, and displays the acquired code. The first-aid information acquisition unit 220 uses the imaged code to acquire first-aid information about an individual associated with the iris image. The first-aid information output unit 230 outputs the first-aid information.

The information output device 200 illustrated in FIG. 5 includes similar configurations to the information output device 200 illustrated in FIG. 1. The information output device 200 is connected to a device having similar functions to the information provision device 300.

The information output device 200 configured in this way uses each configuration to output first-aid information related to a code displayed by the information display device 100.

This is because each configuration in the information output device 200 illustrated in FIG. 5 operates in a similar manner to the configuration in the information output device 200 described with reference to FIG. 1.

The information output device 200 illustrated in FIG. 5 is an example of a minimum configuration of the information output device 200 in the first example embodiment.

[Hardware Configuration]

Next, hardware configurations of the information display device 100, the information output device 200, and the information provision device 300 (hereinafter referred to as "the information display device 100 or the like") will be described.

Each component of the information display device 100 or the like may be constituted by a hardware circuit.

Alternatively, in the information display device 100 or the like, each component may be constituted by a plurality of devices connected via a network.

Alternatively, in the information display device 100 or the like, a plurality of components may be constituted by one piece of hardware.

Alternatively, the information display device 100 or the like may be implemented as a computer that includes a central processing unit (CPU), a read only memory (ROM), and a random access memory (RAM). The information display device 100 or the like may be implemented as a computer that further includes an input and output circuit (IOC) in addition to the configurations described above. The information display device 100 or the like may be implemented as a computer that further includes a network interface circuit (NIC) in addition to the configurations described above.

Figure 6:
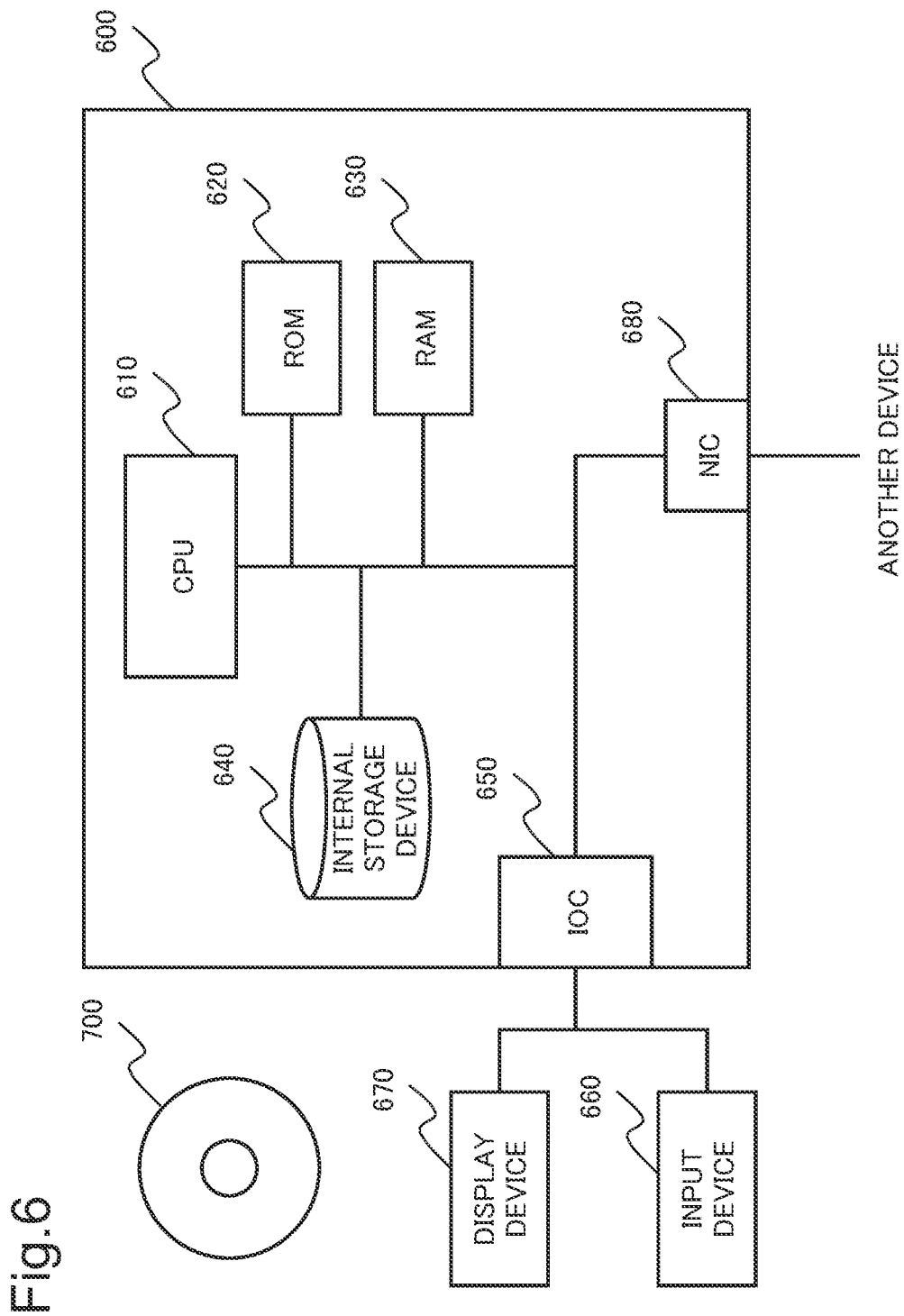
FIG. 6 is a block diagram illustrating a configuration of an information processing device, which is an example of a hardware configuration of the information display device or the like according to the first example embodiment.

FIG. 6 is a block diagram illustrating a configuration of an information processing device 600, which is an example of the hardware configuration of the information display device 100 or the like according to the first example embodiment.

The information processing device 600 includes a CPU 610, a ROM 620, a RAM 630, an internal storage device 640, an IOC 650, and a NIC 680, and constitutes a computer.

The CPU 610 reads a program from the ROM 620 and/or the internal storage device 640. Then, the CPU 610 controls the RAM 630, the internal storage device 640, the IOC 650, and the NIC 680 in accordance with the read program.

Then, the computer that includes the CPU 610 controls these configurations to implement the functions of the information display device 100 or the like illustrated in FIG. 1. For example, the computer that includes the CPU 610 implements the functions as the capture unit 110, the code acquisition unit 120, and the code display unit 130 in the information display device 100. Alternatively, the computer that includes the CPU 610 implements the functions as the capture unit 210, the first-aid information acquisition unit 220, and the first-aid information output unit 230 in the information output device 200. Alternatively, the computer that includes the CPU 610 implements the functions as the information storage unit 310 and the information provision unit 320 in the information provision device 300.

In a case where the function as the capture unit 110 or the capture unit 210 is implemented, the computer that includes the CPU 610 may include an imaging device such as a camera (not illustrated). In this case, the imaging device captures an image of an iris in accordance with an instruction from the CPU 610. For example, the computer that includes the CPU 610 may use an input device 660 described later as an imaging device used for the capture unit 110 or the capture unit 210. In this case, the computer that includes the CPU 610 may include the input device 660. However, the input device 660 may not be included in the computer.

The CPU 610 may implement the functions by using the RAM 630 or the internal storage device 640 as a temporary storage medium for programs.

The CPU 610 may use a storage medium reader (not illustrated) to read a program included in a recording medium 700 in which programs are stored in a computer-readable manner. Alternatively, the CPU 610 may receive a program from an external device (not illustrated) via the NIC 680, store the program in the RAM 630 or the internal storage device 640, and operate in accordance with the stored program.

The ROM 620 stores programs to be executed by the CPU 610 and fixed data. The ROM 620 is, for example, a programmable-ROM (P-ROM) or a flash ROM.

The RAM 630 temporarily stores programs to be executed by the CPU 610 and data. The RAM 630 is, for example, a dynamic-RAM (D-RAM).

The internal storage device 640 stores data and programs to be stored for a long period by the information processing device 600. The internal storage device 640 may operate as a temporary storage device of the CPU 610. The internal storage device 640 is, for example, a hard disk drive, a magneto-optical disk drive, a solid state drive (SSD), or a disk array device.

The ROM 620 and the internal storage device 640 are non-volatile (non-transitory) storage media. On the other hand, the RAM 630 is a volatile (transitory) storage medium. The CPU 610 can be operated in accordance with a program stored in the ROM 620, the internal storage device 640, or the RAM 630. That is, the CPU 610 can be operated by using a non-volatile storage medium or a volatile storage medium.

The IOC 650 mediates data between the CPU 610 and the input device 660, and between the CPU 610 and a display device 670. The IOC 650 is, for example, an I/O interface card or a universal serial bus (USB) card. Furthermore, the IOC 650 is not limited to a wired connection such as a USB connection, and may use a wireless connection.

The input device 660 receives an input instruction from an operator of the information processing device 600. The input device 660 is, for example, a keyboard, a mouse, or a touch panel. The input device 660 may be an imaging device used for the capture unit 110 or the capture unit 210.

The display device 670 presents information to an operator of the information processing device 600. For example, the code display unit 130 may display a code on the display device 670. Alternatively, the first-aid information output unit 230 may output first-aid information to the display device 670. The display device 670 is, for example, a liquid crystal display, an organic electroluminescent display, or electronic paper.

The NIC 680 relays data exchange with the information display device 100 or the like via a network and data exchange between the information display device 100 or the like and an external device (not illustrated). The NIC 680 is, for example, a local area network (LAN) card. Furthermore, the NIC 680 is not limited to a wired connection, and may use a wireless connection.

The information processing device 600 configured in this way can obtain effects similar to those of the information display device 100 or the like.

This is because the CPU 610 of the information processing device 600 can implement similar functions to the information display device 100 or the like in accordance with a program.

Second Example Embodiment

Iris images are sensitive information. For communication of iris images, it is preferable to use a secure communication path. It is preferable that an iris image of an individual be not associated with first-aid information about the individual.

For this reason, as a second example embodiment, a first-aid information provision system 402 in which security of communication of iris images has been improved will be described. However, in the second example embodiment, as in the first example embodiment, a code is not provided when an owner of an information display device 101 is not present.

Congestion of communication paths and the like is expected during a disaster or the like. For this reason, in the second example embodiment, communication for acquiring a code is avoided when the code is displayed.

In the following description, configurations and operations similar to those in the first example embodiment will be omitted as appropriate.

Figure 7:
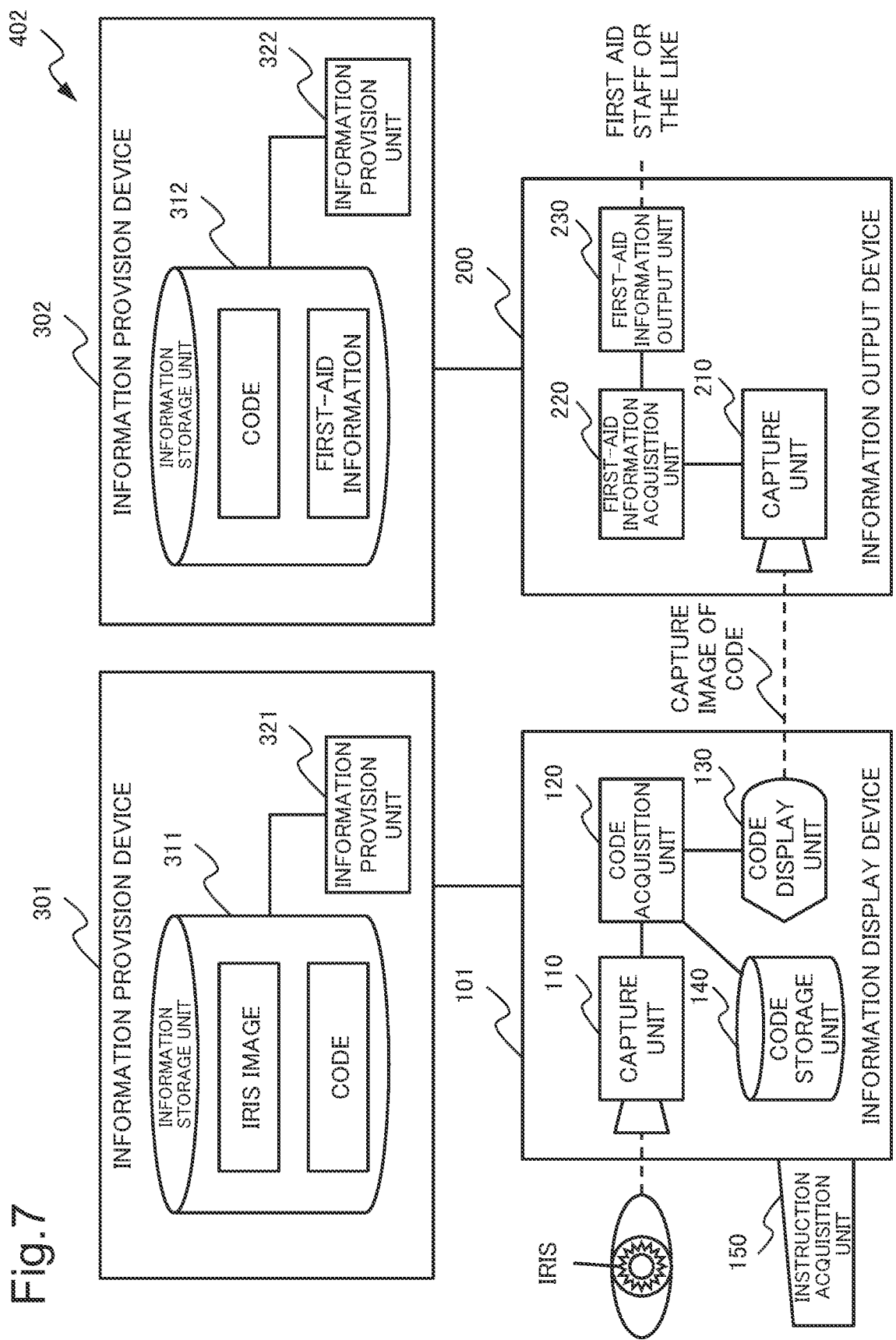
FIG. 7 is a block diagram illustrating an example of a configuration of a first-aid information provision system according to a second example embodiment.

FIG. 7 is a block diagram illustrating an example of a configuration of the first-aid information provision system 402 according to the second example embodiment.

Note that FIG. 7 is not intended to limit the number of pieces of each device included in the first-aid information provision system 402. For example, the first-aid information provision system 402 may include a plurality of the information output devices 200. Each of the devices included in the first-aid information provision system 402 may be constituted by the computer illustrated in FIG. 6. In a case where each device is constituted by the computer, the first-aid information provision system 402 may include an imaging device such as a camera, as necessary.

The first-aid information provision system 402 includes the information display device 101, the information output device 200, an information provision device 301, and an information provision device 302.

The information provision device 301 includes an information storage unit 311 and an information provision unit 321.

The information storage unit 311 stores information to be provided to the information display device 101. In the description of the present example embodiment, the information storage unit 311 stores an iris image and a code in association with each other. However, this is not intended to limit the present example embodiment. The information stored by the information storage unit 311 is not limited to the above.

The information provision unit 321 provides a code associated with an iris image received from the information display device 101 to the information display device 101.

The information provision device 302 includes an information storage unit 312 and an information provision unit 322.

The information storage unit 312 stores first-aid information to be provided to the information output device 200. In the description of the present example embodiment, the information storage unit 312 stores a code and a piece of first-aid information in association with each other. However, this is not intended to limit the present example embodiment. The information stored by the information storage unit 311 is not limited to the above.

The information provision unit 322 provides first-aid information associated with a code received from the information output device 200 to the information output device 200.

The information output device 200 has a configuration similar to that in the first example embodiment. However, the information output device 200 is connected to the information provision device 302. Then, as in the first example embodiment, the information output device 200 acquires first-aid information from the information provision device 302 by using an imaged code, and outputs the acquired first-aid information. The information output device 200 does not need to be connected to the information provision device 301 that stores iris images.

The information display device 101 includes, in addition to a configuration of an information display device 100, a code storage unit 140 and an instruction acquisition unit 150.

A code acquisition unit 120 acquires, from the information provision device 301, a code associated with an iris image captured by an capture unit 110. Then, the code acquisition unit 120 requests the code storage unit 140 to store the acquired code and the iris image.

The code acquisition unit 120 may generate a code in accordance with the iris image captured by the capture unit 110, and store the generated code in the code storage unit 140. In this case, it is preferable that the information display device 101 be able to stop regeneration of the code in order to prevent unauthorized regeneration of the code.

Furthermore, the code acquisition unit 120 captures an iris image in accordance with an instruction, uses the captured iris image to acquire a code stored in the code storage unit 140, and displays the acquired code on a code display unit 130.

The code storage unit 140 stores a code and an iris image.

The code storage unit 140 may store a plurality of iris images and codes associated with them. In this case, the code storage unit 140 stores an iris image and a code in association with each other.

Furthermore, the number of codes to be stored in association with an iris image by the code storage unit 140 is not limited to one, and may be two or more. In this case, the code acquisition unit 120 may select a code to be acquired for display from a plurality of codes in accordance with a selection rule. For example, the code acquisition unit 120 may randomly select a code each time a code is displayed.

Furthermore, there is no limitation on the timing at which the code acquisition unit 120 changes the code to be displayed. For example, the code acquisition unit 120 may change the code when the number of times the code has been displayed exceeds a predetermined number. Alternatively, the code acquisition unit 120 may change the code at a predetermined time interval.

The instruction acquisition unit 150 acquires an instruction for a series of operations described next. The series of operations include an operation of capturing an iris image by the capture unit 110, an operation of acquiring a code associated with the captured iris image from the code storage unit 140 by the code acquisition unit 120, and an operation of displaying the acquired code by the code display unit 130.

The instruction acquisition unit 150 is, for example, a switch, a key, or a touch panel in the information display device 101. Alternatively, the instruction acquisition unit 150 may be an acceleration sensor or a rotation sensor included in the information display device 101.

The information display device 101 operates as described below in detail.

The information display device 101 uses the capture unit 110 to capture an image of an iris in advance, uses the code acquisition unit 120 to acquire a code associated with the iris image from the information provision device 301, and stores the iris image and the code in the code storage unit 140. For example, the information display device 101 stores an iris image of the owner of the information display device 101 and a code associated with the iris image.

The communication path used by the information display device 101 to acquire a code from the information provision device 301 is preferably a secure communication path (e.g., a direct connection using a cable or the like, a dedicated line, or a secure intranet connection in a facility).

Then, the code acquisition unit 120 requests the capture unit 110 to capture an image of an iris in accordance with an instruction from the instruction acquisition unit 150, and acquires an iris image.

Then, the code acquisition unit 120 acquires, from codes stored in the code storage unit 140, a code associated with an iris image that matches the captured iris image.

Match determination by the code acquisition unit 120 may include a match in a certain range in addition to an identical match, as in the match determination by the information provision unit 320. The code acquisition unit 120 may acquire a code associated with an iris image that matches the captured iris image in a predetermined range.

In a case where the code storage unit 140 stores a plurality of iris images, the code acquisition unit 120 uses a predetermined method to acquire a code associated with an iris image that most matches the captured iris image. For match determination in this case, the code acquisition unit 120 may use a determination similar to the iris image match determination by the information provision unit 320.

For example, the code acquisition unit 120 may select an iris image that most matches the captured iris image and acquire a code associated with the selected iris image.

In a case where the code storage unit 140 stores one iris image, the code acquisition unit 120 acquires a code in a case where the captured iris image matches the stored iris image. In this case, the information display device 101 serves as a device for displaying the code associated with the individual relevant to the iris. In a case where the information display device 101 is used as a device for an individual, the iris image stored in the code storage unit 140 is not limited to one iris image. For example, the code storage unit 140 may store iris images of two eyes (left eye and right eye) of an individual and codes associated with the iris images.

Then, the code display unit 130 displays the code acquired by the code acquisition unit 120.

In this way, in a case where an iris image captured when the instruction acquisition unit 150 has acquired an instruction matches an iris image that has been stored in advance, the information display device 101 displays a code associated with the iris image. Thus, the information display device 101 can avoid display of a code in a case where an iris image cannot be captured due to, for example, a person associated with a stored iris image being not present. The person associated with the stored iris image is, for example, the owner of the information display device 101.

The communication path and the communication partner (information provision device 302) used by the information output device 200 to acquire first-aid information from a code are different from the communication path and the communication partner (information provision device 301) used by the information display device 101 to acquire a code from an iris image. Thus, the information output device 200 cannot acquire an iris image even by using a code.

Furthermore, in a case where the first-aid information provision system 402 uses a highly secure communication path as the communication path between the information display device 101 and the information provision device 301, the first-aid information provision system 402 can further reduce the possibility of leakage of iris images.

For a code stored in the code storage unit 140, the information display device 101 may set a limitation on a code storage period or the number of times of acquisition by the code acquisition unit 120. For example, in a case where the code acquisition unit 120 has acquired a code a predetermined number of times, the information display device 101 may delete the code stored in the code storage unit 140 and request a user of the information display device 101 or the like to acquire a code again.

[Description of Effects]

Next, effects of the first-aid information provision system 402 according to the second example embodiment will be described.

The first-aid information provision system 402 according to the second example embodiment can provide an effect of improving the security of iris images in addition to the effects of the first example embodiment.

This is because the information output device 200 uses a communication path different from the communication path for the information display device 101 to receive a code by using an iris image as the communication path for acquiring first-aid information by using a code.

In a case where the information display device 101 uses a highly secure communication path as a path for acquiring a code, the first-aid information provision system 402 can further improve the security of communication of iris images.

The first-aid information provision system 402 has an effect of protecting a code in a case where a person associated with an iris image stored in the information display device 101 is not present. This is because the information display device 101 displays a code related to an iris image captured in accordance with an instruction from the instruction acquisition unit 150.

Third Example Embodiment

An identifier (ID) is widely used as information for identifying an individual. For this reason, a first-aid information provision system 400 may use an iris image and an identifier in combination.

Thus, as a third example embodiment, an example of a case in which an identifier is used will be described.

FIG. 8 is a block diagram illustrating an example of a configuration of a first-aid information provision system 403 according to the third example embodiment.

Note that FIG. 8 is not intended to limit the number of pieces of each device included in the first-aid information provision system 403. For example, the first-aid information provision system 403 may include a plurality of information output devices 200. Each of the devices included in the first-aid information provision system 403 may be constituted by the computer illustrated in FIG. 6. In a case where each device is constituted by the computer, the first-aid information provision system 403 may include an imaging device such as a camera, as necessary.

The first-aid information provision system 403 includes an information display device 102, the information output device 200, and an information provision device 303.

The information provision device 303 includes an information storage unit 313 and an information provision unit 323.

The information storage unit 313 includes an iris image, an identifier (ID), a code, and first-aid information.

The information storage unit 313 stores the iris image and the ID in association with each other. For example, the information provision device 303 identifies an individual by using image authentication or the like on an acquired iris image, associates an ID of the identified individual with the iris image, and stores them in the information storage unit 313. Alternatively, the information provision device 303 may acquire an iris image, an ID, and information for associating them from a device (not illustrated), and store the iris image and the ID in association with each other.

Furthermore, the information storage unit 313 stores an ID and a code in association with each other.

Furthermore, the information storage unit 313 stores a code and a piece of first-aid information in association with each other.

In the present example embodiment, a code may be generated by using, as original data of the code, data in which an iris image and an ID are combined. In this way, a code may be generated from information in which an iris image and another piece of information related to the individual are combined. An iris image is information that is at least partially unstable. On the other hand, an ID is information that does not change. Thus, in a case where a code is generated by using an ID, the generated code is more stable than in a case where a code is generated by using an iris image. In other words, in a case where a code is generated by using an ID, a code matching accuracy is improved.

The first-aid information provision system 403 may use authentication data as code authentication. That is, the first-aid information provision system 403 may receive authentication data in addition to a code as information received by the information provision device 303 from the information output device 200.

The first-aid information provision system 403 may use, as authentication data, for example, a hash obtained by applying an ID to a hash function.

However, authentication data is not limited to a hash of an ID. For example, a generated code may include a part of an ID (e.g., a predetermined number of higher or lower order bits). In this case, the first-aid information provision system 403 may directly use, as authentication data, bits of the ID not included in the code. The information provision device 303 can authenticate the code on the basis of a comparison between the ID and a combination of bits included in the code and bits included in the authentication data.

The information provision unit 323 provides information to the information display device 102 and the information output device 200.

When compared with the information display device 100 in the first example embodiment, the information display device 102 includes a code acquisition unit 121 instead of the code acquisition unit 120, and further includes an ID acquisition unit 160.

The ID acquisition unit 160 uses an iris image from an capture unit 110 to acquire an ID from the information provision device 303. The ID acquisition unit 160 may be called an identifier acquisition unit.

The code acquisition unit 121 uses an ID to acquire a code from the information provision device 303.

The code display unit 130 displays a code.

The information output device 200 operates in a similar manner to the information output device 200 in the first example embodiment.

In a case where the first-aid information provision system 403 uses authentication data, each device operates as follows, for example.

The information display device 102 acquires authentication data in addition to a code from the information provision device 303. Then, the information display device 102 provides the authentication data to the information output device 200. For example, the information display device 102 uses short-range communication to provide the authentication data to the information output device 200. A code is displayed on a display device, and can therefore be imaged from a distant location. However, authentication data cannot be acquired from a distant location. In this way, authentication data is secure in a different way from codes.

The information output device 200 transmits, to the information provision device 303, the authentication data acquired from the information display device 102 in accordance with the code.

The information provision device 303 authenticates the information output device 200 by using the code and the authentication data. Then, the information provision device 303 provides first-aid information to the information output device 200 that has been authenticated.

[Description of Effects]

Next, effects of the first-aid information provision system 403 according to the third example embodiment will be described.

The first-aid information provision system 403 has an effect of improving the code matching accuracy in addition to the effects of the first example embodiment.

This is because the first-aid information provision system 403 generates a code by using an ID in addition to an iris image.

Furthermore, in a case where authentication data is used, the first-aid information provision system 403 has an effect of further improving security of provision of first-aid information.

An identifier (ID) is widely used in a general information processing system. For example, for the first-aid information provision system 403, it is possible to achieve necessary main configurations by adding a configuration related to iris images to a general information processing system. That is, the first-aid information provision system 403 has an effect of being easier to be constructed from a general information processing system as compared with the first example embodiment or the like.

Fourth Example Embodiment

Even for the same individual, first-aid information necessary for first aid for the individual varies depending on the organization related to first aid. For example, in a case of an evacuee from a disaster, contact information is needed to contact a family member or the like, and information regarding allergies and the like is needed in a case where a meal is provided.

For this reason, as a fourth example embodiment, an example embodiment in which first-aid information to be output is changed in relation to each of information output devices 201 will be described.

In the following description, an authority for a range of first-aid information that can be acquired is set for each information output device 201. A method of setting authorities to the information output devices 201 is not restrictive. For example, each of the information output devices 201 may store the authority. Alternatively, the authorities may be stored in a device (e.g., a gateway) that serves as a point of contact with outside of an organization in which an information output device 200 is provided. That is, a system of the organization that includes the information output device 200 may store the authorities. In the following description, by way of example, each of the information output devices 201 stores the authorities.

FIG. 9 is a block diagram illustrating an example of a configuration of a first-aid information provision system 404 according to the fourth example embodiment.

Note that FIG. 9 is not intended to limit the number of pieces of each device included in the first-aid information provision system 404. For example, the first-aid information provision system 404 may include a plurality of the information output devices 201. Each of the devices included in the first-aid information provision system 404 may be constituted by the computer illustrated in FIG. 6. In a case where each device is constituted by the computer, the first-aid information provision system 404 may include an imaging device such as a camera, as necessary.

The first-aid information provision system 404 includes an information display device 100, the information output device 201, and an information provision device 304.

The information provision device 304 includes an information storage unit 314 and an information provision unit 324.

The information storage unit 314 further stores authority information in addition to information similar to that in the information storage unit 310 in the first example embodiment.

The authority information is information in which an authority relating to first-aid information (hereinafter referred to simply as the "authority") is associated with a range of first-aid information for the authority.

When receiving a code from the information output device 201, the information provision unit 324 receives the authority set for the information output device 201. Then, the information provision unit 324 uses the authority information to provide first-aid information within the range of the received authority to the information output device 201.

The information display device 100 displays a code associated with an iris image in a similar manner to the information display device 100 in the first example embodiment.

The information output device 201 includes, in addition to the configurations included in the information output device 200, an authority storage unit 240.

The authority storage unit 240 stores the authority set for the information output device 200.

A first-aid information acquisition unit 220 transmits an imaged code and an authority to the information provision device 304.

For example, an example of a case will be described in which the first-aid information provision system 404 includes an information output device 201 provided in a medical institution and an information output device 201 provided in a lost child center.

The information output device 201 provided in the medical institution stores an authority "medical care".

The information output device 201 provided in the lost child center stores an authority "lost child".

The information provision device 304 stores, as authority information, the range of first-aid information for the authority "medical care" (hereinafter referred to as the "range of medical care") and the range of first-aid information for the authority "lost child" (hereinafter referred to as the "range of lost child").

In a case where the information provision device 304 has received a code and the authority "medical care" from the information output device 201, the information provision device 304 transmits, to the information output device 201, information (e.g., treatment history, medication history, and allergy information) included in the "range of medical care" among pieces of first-aid information associated with the code.

On the other hand, in a case where the information provision device 304 has received a code and the authority "lost child" from the information output device 201, the information provision device 304 transmits, to the information output device 201, information (e.g., a parent's telephone number, email address, or address) included in the "range of lost child" among pieces of first-aid information associated with the code.

In this way, the first-aid information provision system 404 uses an authority to limit the range of information to be provided to the information output device 201.

The information provision device 304 may store authority information related to each of the information output devices 201 in advance. In this case, the information output device 201 may not include the authority storage unit 240.

[Description of Effects]

Next, effects of the first-aid information provision system 404 according to the fourth example embodiment will be described.

The first-aid information provision system 404 has, in addition to the effects of the first example embodiment, an effect of setting the range of first-aid information provided to the information output device 201 in accordance with the authority set for the information output device 201.

This is because the information provision device 304 transmits first-aid information in the range related to the authority received from the information output device 201 or the authority set for the information output device 201.

Fifth Example Embodiment

Left and right irises are different. That is, for each individual, there are two iris images for identifying the individual. For this reason, as a fifth example embodiment, an example embodiment in which two iris images of an individual are used will be described.

In the following description of the fifth example embodiment, the first-aid information provision system 400 illustrated in FIG. 1 will be used. However, this is not intended to limit the fifth example embodiment to the first-aid information provision system 400 illustrated in FIG. 1. The fifth example embodiment may be applied to the second to fourth example embodiments.

In the following description, configurations and operations similar to those in the first example embodiment will be omitted, and matters specific to the fifth example embodiment will be described. In the following description, an image associated with an iris of one eye is referred to as an "iris image of one eye", and a code associated with an iris image of one eye is referred to as a "code of one eye". An image associated with irises of both eyes is called an "iris image of both eyes" and a code associated with an iris image of both eyes is called a "code of both eyes". The same applies to a left eye and a right eye.

In general, acquiring an iris image of both eyes requires more processing time than acquiring an iris image of one eye. In a time of emergency, it is desirable to save even a little time in some cases. For a victim of an accident or the like, a case can be assumed in which an iris image of only one eye with a wound can be acquired.

For this reason, by way of example, a case will be described in which concise first-aid information required in a time of emergency or the like is output in a case where a code of one eye has been acquired, and more detailed first-aid information is output in a case where a code of both eyes has been acquired.

The information display device 100 captures an image of an iris of one eye or irises of both eyes in response to an instruction (e.g., a key operation) from an operator of the information display device 100, and displays a code of one eye or a code of both eyes. Here, the operator is not limited to the owner of the information display device 100. For example, the operator is a rescue worker.

The information output device 200 captures the code displayed by the information display device 100, and transmits the imaged code to the information provision device 300.

The information provision unit 320 of the information provision device 300 determines whether the received code is a code of one eye or a code of both eyes, and changes first-aid information to be provided to the information output device 200 in accordance with a result of the determination.

For example, in a case where a code of one eye has been received, the information provision unit 320 provides concise first-aid information necessary for first aid or the like. On the other hand, in a case where a code of both eyes has been received, the information provision unit 320 provides, as first-aid information, information necessary for medication and/or detailed first-aid information necessary for hospitalization or the like.

In this way, the first-aid information acquired by the first-aid information acquisition unit 220 by using the code of one eye is at least partially different from the first-aid information acquired by using the code of both eyes. The "different" in this case includes the presence or absence of information, that is, a case where there is an inclusion relation between the pieces of first-aid information.

Alternatively, the first-aid information provision system 400 may distinguish between a code of the right eye and a code of the left eye. In this case, the information provision unit 320 may change the first-aid information to be provided on the basis of the distinction between right and left of the code. For example, in a case where the owner of the information display device 100 regularly visits two clinical departments, the information provision unit 320 may provide first-aid information regarding one of the clinical departments for the code of the left eye, and may provide first-aid information regarding the other clinical department for the code of the right eye.

Alternatively, for example, in a case of a traffic accident or the like, the information provision unit 320 may provide first-aid information necessary for a police officer for a code of the left eye of a victim, and may provide first-aid information necessary for a rescue worker for a code of the right eye of the victim.

The first-aid information provision system 400 may use a combination of the three codes described above, that is, the code of the left eye, the code of the right eye, and the code of both eyes.

[Description of Effects]

Next, effects of the fifth example embodiment will be described.

The fifth example embodiment has, in addition to the effects of the first example embodiment, an effect of allowing first-aid information provided to the information output device 200 to be changed in accordance with the eyes used.

This is because of the following reasons.

The information display device 100 displays a code of one eye or a code of both eyes. Alternatively, the information display device 100 displays a code of the left eye or a code of the right eye. The information provision device 300 changes the first-aid information to be provided in accordance with which eye the code received from the information output device 200 is associated with.

For example, the first-aid information provision system 400 according to the fifth example embodiment can provide first-aid information relevant to a plurality of clinical departments regarding the owner of the information display device 100.

The example embodiments may be used in combination.

Some or all of the above example embodiments may be described as the following Supplementary Notes, but are not limited to the following.

(Supplementary Note 1)

A first-aid information provision system including:

an information display device that includes first capture means for capturing an iris image, code acquisition means for acquiring a code associated with the captured iris image, and code display means for displaying the acquired code; and an information output device that includes second capture means for imaging the code displayed by the information display device, first-aid information acquisition means for acquiring first-aid information about an individual associated with the iris image by using the imaged code, and first-aid information output means for outputting the first-aid information.

(Supplementary Note 2)

The first-aid information provision system according to Supplementary Note 1, in which the first-aid information output means transmits information to another device in accordance with the first-aid information.

(Supplementary Note 3)

The first-aid information provision system according to Supplementary Note 1 or 2, in which the information display device further includes:

code storage means for storing the iris image and the code in association with each other; and instruction acquisition means for acquiring an instruction to display the code, the first capture means captures the iris image in accordance with the instruction, and the code acquisition means acquires the code associated with the iris image that matches the captured iris image in a predetermined range among the iris images stored in the code storage means.

(Supplementary Note 4)

The first-aid information provision system according to any one of Supplementary Notes 1 to 3, in which the information output device has an authority relating to the first-aid information, and the first-aid information acquisition means acquires the first-aid information related to the authority.

(Supplementary Note 5)

The first-aid information provision system according to any one of Supplementary Notes 1 to 4, in which the information display device further includes identifier acquisition means for acquiring an identifier of the individual by using the iris image, and the code acquisition means acquires the code by using the acquired identifier.

(Supplementary Note 6)

The first-aid information provision system according to Supplementary Note 5, in which the code includes at least a part of the identifier.

(Supplementary Note 7)

The first-aid information provision system according to any one of Supplementary Notes 1 to 6, in which the code acquisition means acquires the code of one eye in a case where the first capture means has captured the iris image of the one eye, and acquires the code of both eyes in a case where the first capture means has captured the iris image of the both eyes, and the first-aid information acquisition means acquires, in a case where the second capture means has imaged the code of the both eyes, the first-aid information that is at least partially different from the first-aid information acquired in a case where the second capture means has imaged the code of the one eye.

(Supplementary Note 8)

The first-aid information provision system according to Supplementary Note 7, in which the code acquisition means acquires the code of a left eye in a case where the first capture means has captured the iris image of the left eye, and acquires the code of a right eye in a case where the first capture means has captured the iris image of the right eye, and the first-aid information acquisition means acquires, in a case where the second capture means has imaged the code of the left eye, the first-aid information that is at least partially different from the first-aid information acquired in a case where the second capture means has imaged the code of the right eye.

(Supplementary Note 9)

The first-aid information provision system according to any one of Supplementary Notes 1 to 8, in which the code is a one-dimensional code or a two-dimensional code.

(Supplementary Note 10)

The first-aid information provision system according to any one of Supplementary Notes 1 to 9, further including an information provision device that provides the code in accordance with the iris image, and provides the first-aid information in accordance with the code.

(Supplementary Note 11)

The first-aid information provision system according to any one of Supplementary Notes 1 to 10, in which the code has less information than the iris image.

(Supplementary Note 12)

An information display device including:

first capture means for capturing an iris image;

code acquisition means for acquiring a code associated with the captured iris image; and code display means for displaying the acquired code as the code imaged by an information output device that captures the code, acquires first-aid information about an individual associated with the iris image by using the imaged code, and outputs the first-aid information.

(Supplementary Note 13)

An information output device including:

second capture means for imaging a code displayed by an information display device that captures an iris image, acquires the code associated with the captured iris image, and displays the acquired code;

first-aid information acquisition means for acquiring first-aid information about an individual associated with the iris image by using the imaged code; and first-aid information output means for outputting the first-aid information.

(Supplementary Note 14)

A first-aid information provision method in a first-aid information provision system that includes an information display device and an information output device, the method including:

by the information display device, capturing an iris image;

acquiring a code associated with the captured iris image; and displaying the acquired code, and by the information output device, imaging the code displayed by the information display device;

acquiring first-aid information about an individual associated with the iris image by using the imaged code; and outputting the first-aid information.

(Supplementary Note 15)

A first-aid information provision method including:

by an information display device, capturing an iris image;

acquiring a code associated with the captured iris image; and displaying the acquired code as the code to be imaged by an information output device that captures the code, acquires first-aid information about an individual associated with the iris image by using the imaged code, and outputs the first-aid information.

(Supplementary Note 16)

A first-aid information provision method including:

by an information processing device, imaging a code displayed by an information display device that captures an iris image, acquires the code associated with the captured iris image, and displays the acquired code;

acquiring first-aid information about an individual associated with the iris image by using the imaged code; and outputting the first-aid information.

(Supplementary Note 17)

A recording medium that records a program that causes a computer to cause an information display device to execute:

processing of capturing an iris image;

processing of acquiring a code associated with the captured iris image; and processing of displaying the acquired code as the code imaged by an information output device that captures the code, acquires first-aid information about an individual associated with the iris image by using the imaged code, and outputs the first-aid information.

(Supplementary Note 18)

A recording medium that records a program that causes an information processing device to execute:

processing of imaging a code displayed by an information display device that captures an iris image, acquires the code associated with the captured iris image, and displays the acquired code;

processing of acquiring first-aid information about an individual associated with the iris image by using the imaged code; and processing of outputting the first-aid information.

While the disclosure has been particularly shown and described with reference to exemplary embodiments thereof, the disclosure is not limited to these embodiments. It will be understood by those of ordinary skill in the art that various changes in form and details may be made therein without departing from the spirit and scope of the example embodiments as defined by the claims.

INDUSTRIAL APPLICABILITY

The example embodiments can be used in medical facilities such as hospitals and clinics, government offices such as government agencies and public offices, and transportation facilities such as airports and stations.

REFERENCE SIGNS LIST 100 information display device
101 information display device
102 information display device
110 capture unit
120 code acquisition unit
121 code acquisition unit
130 code display unit
140 code storage unit
150 instruction acquisition unit
160 ID acquisition unit
200 information output device
201 information output device
210 capture unit
220 first-aid information acquisition unit
230 first-aid information output unit
240 authority storage unit
300 information provision device
301 information provision device
302 information provision device
303 information provision device
304 information provision device
310 information storage unit
311 information storage unit
312 information storage unit
313 information storage unit
314 information storage unit
320 information provision unit
321 information provision unit
322 information provision unit
323 information provision unit
324 information provision unit
400 first-aid information provision system
401 first-aid information provision system
402 first-aid information provision system
403 first-aid information provision system
404 first-aid information provision system
600 information processing device
610 CPU
620 ROM
630 RAM
640 internal storage device
650 IOC
660 input device
670 display device
680 NIC
700 recording medium

What is claimed is:

1. A first-aid information provision system comprising:
a memory configured to store instructions; and
at least one processor configured to execute the instructions to perform:
controlling first capture means device for capturing an iris image;
acquiring a code associated with the captured iris image;
displaying the acquired code;
controlling second capture means device for imaging the code;

acquiring first-aid information about an individual associated with the iris image by using the imaged code;

outputting the first-aid information; and storing the iris image and the code in association with each other; wherein the at least one processor is configured to execute the instructions to perform:

acquiring an instruction to display the code;

controlling the first capture means device captures the iris image in accordance with the instruction; and acquiring the code associated with the iris image that matches the captured iris image in a predetermined range among the stored iris images.

2. The first-aid information provision system according to claim 1, wherein the at least one processor is configured to execute the instructions to perform:

transmitting information to another device in accordance with the first-aid information.

3. The first-aid information provision system according to claim 1, wherein the at least one processor is configured to execute the instructions to perform:

acquiring the first-aid information related to an authority of the information output device.

4. The first-aid information provision system according to claim 1, wherein the at least one processor is configured to execute the instructions to perform:

acquiring an identifier of the individual by using the iris image, and acquiring the code by using the acquired identifier.

5. The first-aid information provision system according to claim 4, wherein the code includes at least a part of the identifier.

6. The first-aid information provision system according to claim 1, wherein the at least one processor is configured to execute the instructions to perform:

acquiring the code of one eye in a case where the first capture means device has captured the iris image of the one eye, and acquires the code of both eyes in a case where the first capture means device has captured the iris image of the both eyes, and acquiring, in a case where the second capture means device has imaged the code of the both eyes, the first-aid information that is at least partially different from the first-aid information acquired in a case where the second capture means device has imaged the code of the one eye.

7. The first-aid information provision system according to claim 6, wherein the at least one processor is configured to execute the instructions to perform:

acquiring the code of a left eye in a case where the first capture means device has captured the iris image of the left eye, and acquires the code of a right eye in a case where the first capture means device has captured the iris image of the right eye, and acquiring, in a case where the second capture means device has imaged the code of the left eye, the first-aid information that is at least partially different from the first-aid information acquired in a case where the second capture means device has imaged the code of the right eye.

8. The first-aid information provision system according to claim 1, wherein the code is a one-dimensional code or a two-dimensional code.

9. The first-aid information provision system according to claim 1, further comprising an information provision device that provides the code in accordance with the iris image, and provides the first-aid information in accordance with the code.

10. The first-aid information provision system according to claim 1, wherein the code has less information than the iris image.

11. A first-aid information provision method in a first-aid information provision system that includes an information display device and an information output device, the method comprising:

by the information display device:

capturing an iris image;

acquiring a code associated with the captured iris image; and displaying the acquired code; and by the information output device:

imaging the code displayed by the information display device;

acquiring first-aid information about an individual associated with the iris image by using the imaged code; and outputting the first-aid information, and storing the iris image and the code in association with each other;

acquiring an instruction to display the code;

controlling the first capture means device captures the iris image in accordance with the instruction; and acquiring the code associated with the iris image that matches the captured iris image in a predetermined range among the stored iris images.

12. A non-transitory recording medium that records a program that causes an information display device to execute:

processing of capturing an iris image;

processing of acquiring a code associated with the captured iris image; and processing of displaying the acquired code as the code imaged by an information output device that captures the code, acquires first-aid information about an individual associated with the iris image by using the imaged code, and outputs the first-aid information; and processing of storing the iris image and the code in association with each other;

processing of acquiring an instruction to display the code;

processing of controlling the first capture means device captures the iris image in accordance with the instruction; and processing of acquiring the code associated with the iris image that matches the captured iris image in a predetermined range among the stored iris images.

* * * * *